United States Patent [19]

MacDonald

[11] Patent Number: 5,044,723
[45] Date of Patent: Sep. 3, 1991

[54] TAPERED FIBRE SENSOR

[75] Inventor: Robert I. MacDonald, Edmonton, Canada

[73] Assignee: Alberta Telecommunications Research Centre, Edmonton, Canada

[21] Appl. No.: 504,868

[22] Filed: Apr. 5, 1990

[51] Int. Cl.$^5$ .............................................. G02B 6/16
[52] U.S. Cl. ..................................... 385/12; 356/128
[58] Field of Search ............... 350/96.26, 96.29, 96.15

[56] References Cited

U.S. PATENT DOCUMENTS

| | | | |
|---|---|---|---|
| 4,560,248 | 12/1985 | Cramp et al. | 350/96.29 X |
| 4,737,004 | 4/1988 | Amitay et al. | 350/96.16 X |
| 4,763,976 | 8/1988 | Nolan et al. | 350/96.20 X |
| 4,798,438 | 1/1989 | Moore et al. | 350/96.29 X |
| 4,824,195 | 4/1989 | Khoe | 350/96.15 X |

*Primary Examiner*—John D. Lee
*Assistant Examiner*—Phan T. Heartney
*Attorney, Agent, or Firm*—Anthony R. Lambert

[57] ABSTRACT

A fibre sensor used for the measurement of ambient refractive index has a tapered end. The taper of the optical fibre generates cladding modes which undergo multiple reflections at the external surface of the fibre, and therefore gives high sensitivity to the ambient index. A tapered fibre is also relatively immune to contamination by adhering droplets when the end reflection is used since the droplets tend to move to the point of greatest radius, which tends to be away from the point where the Fresnel reflection of interest occurs. The reflection from the tapered end of a multimode fibre is measured as a function of ambient refractive index. In contrast to a square-cleaved fibre, the reflection from a tapered fibre is monotonically related to the ambient index, removing an ambiguity that occurs when refractive index is measured by Fresnel reflection at normal incidence. Tapered optical fibres are suitable for probes to identify the interface between immiscible liquids.

8 Claims, 5 Drawing Sheets

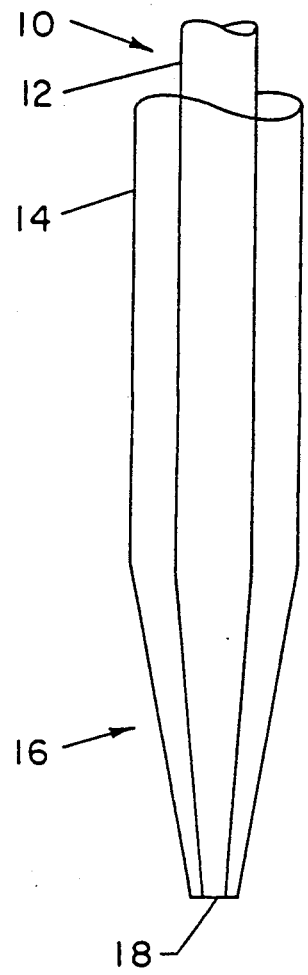
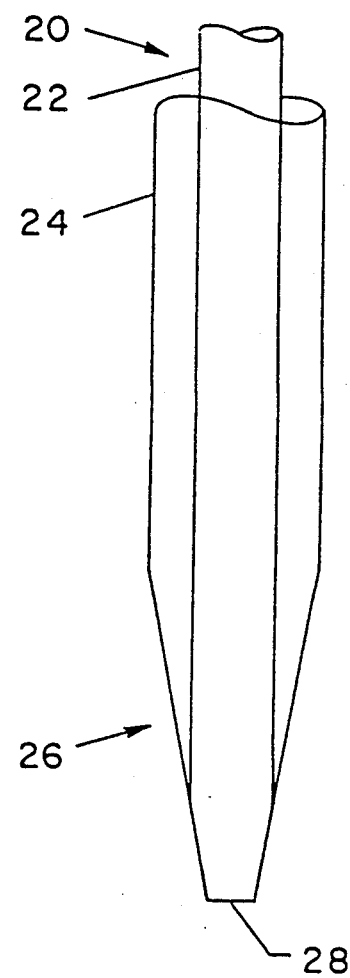
FIGURE 1
FIGURE 2

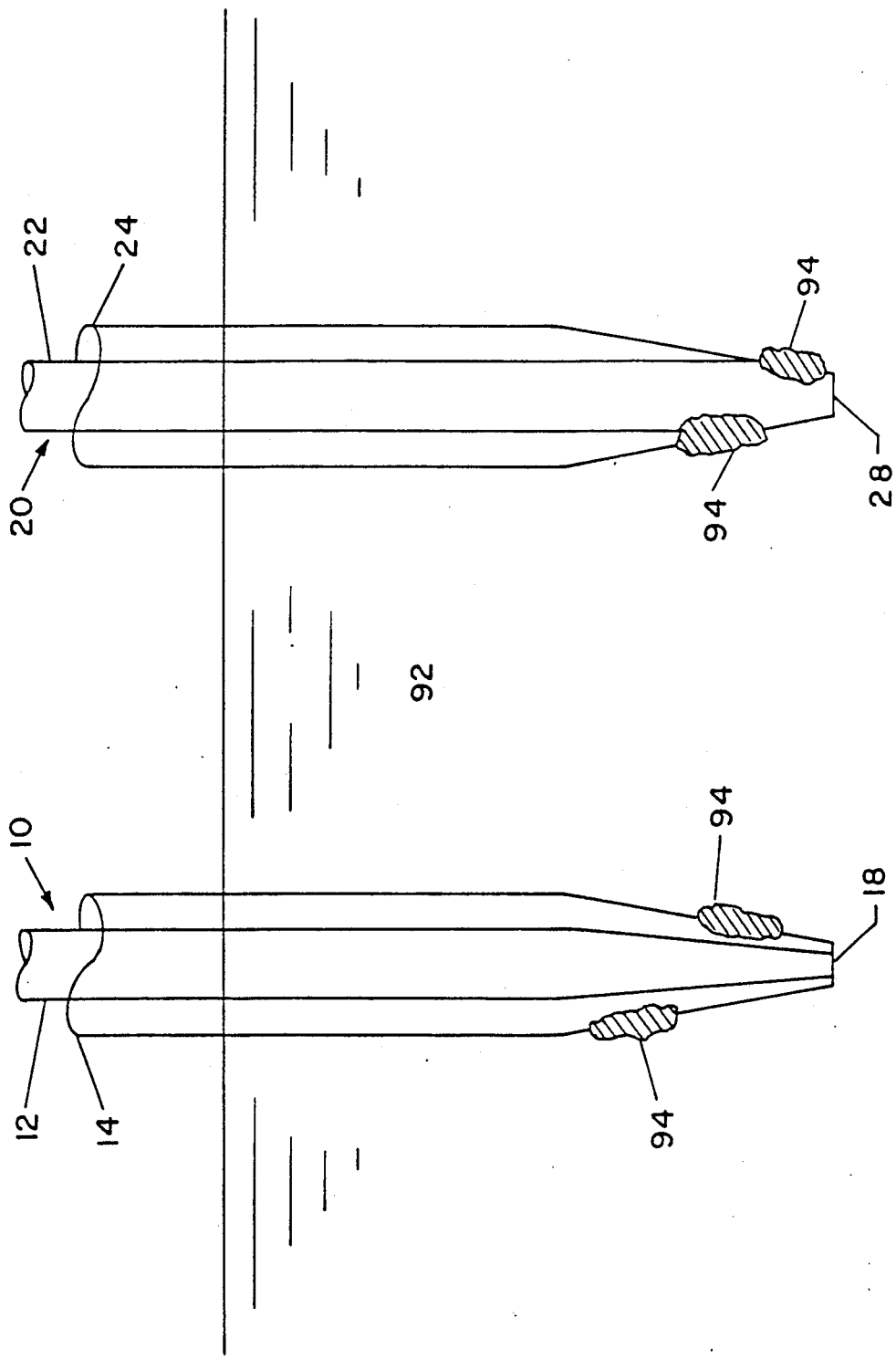

TAPERED FIBRE SENSOR

FIELD OF INVENTION

This invention relates to fibre sensors used in the determination of refractive index of a liquid.

BACKGROUND OF THE INVENTION

Measurement of the Fresnel reflection at the end of an optical fibre provides a very convenient method of determining the refractive index of fluids. The measurement volume is very small, the fibre probe is inert and passive, and the measurement can be made with good sensitivity by fibre reflectometry. The technique has been examined for applications in medicine, where it can employ the dependence of fluid refractive index on a number of parameters of medical interest, such as chemical composition and pressure.

Of particular interest to petrochemical operations is the remote identification of interfaces between immiscible fluids. In this situation, however, the type of fibre probe used in the above work presents problems. Square-cleaved fibres are not suitable as sensors of the passage of an interface between immiscible fluids because of the tendency for droplets of one or the other fluid to adhere to the end surface of the fibre. In most cases such droplets are thick enough to dominate the end reflection so that the transfer of the fibre end to the other fluid is not detectable. This phenomenon is noticeable in such a simple case as the immersion of a fibre in water and its subsequent withdrawal to air. In general, the droplet which forms on the end must be removed or allowed to evaporate in order to observe the Fresnel air reflection from the fibre end.

Tapered optical fibres are known, but optical fibres having the tapers described here for use as fibre optical sensors are not known.

For example, reflections from a 45 degree taper have been used previously to measure gas void fractions in fluids, the taper serving in effect as a corner reflector. Spindler et al, Faseroptischer Sensor zur Messung des ortlichen Gasgehaltes in Flussigkeiten, Tecnisches Messen tm54, pp. 50–55, shows a tapered fibre that is useful to detect the rather large index difference between fluids and gases. At this particular angle the taper acts like a cornercube reflector and sends the light back directly the way it came after exactly two bounces. The taper is so abrupt t hat it cannot function as in the present invention to cause an interaction between the light and the external medium at the cladding boundary. It is useful only for detecting rather large index differences in the external medium, such that for one medium the 45 degree incidence angle is greater than or near the critical angle, while for another medium it is less than the critical angle. The taper is not used to keep the probe clear of contamination. Such a taper appears too steep to be effective for use to enhance the dependence of the reflections on the external refractive index or to remove the problem of adhering droplets, as described in this patent. In the present invention, the tapers are considerably shallower, around 20 degrees, and are preferably formed by drawing down the fibre.

Tapered fibres are also known for connection of two optical fibres to each other or for coupling radiation from a light source into a fibre. However, the purpose of those fibres is different and the advantages of the present fibre would not have been obvious from knowledge of the existence of those tapered fibres.

In particular, fibres tapered for input coupling purposes possess flat or bulbous ends whereas the tapered optical fibres of the present invention can function when the taper extends to a point. The taper angle for the optical fibre sensor described here is determined on a different basis than for a coupler. The angle in the optical fibre sensor of the present invention must be chosen to provide large numbers of cladding boundary reflections without reducing the overall reflection below what can be detected in a particular application. The taper input coupler, on the other hand, maximizes the input coupling of radiation. In general, the tapered optical fibre of the present invention requires smaller taper angles than taper input couplers.

Biconical tapers are also known for coupling light laterally between two or more fibres. These differ from the present invention because the tapers do not terminate in ends, but reverse, so that they expand back to the original fibre size. The reversal of the direction of the light is undesirable in these devices, and the tapers are formed so as to prevent it.

The tapered fibre of the present invention provides several unexpected advantages over these prior art tapers, including that the core taper allows the unbound propagating modes to interact more often at the interface with the external medium and that droplets of another medium tend to adhere away from the interface where the Fresnel reflection of interest occurs. These advantages will now be described in more detail.

SUMMARY OF THE INVENTION

The present invention seeks to enhance the detection of boundaries between immiscible fluids by measurement of the end reflection of fibres immersed in these fluids. The optical fibre used in the measurement is tapered rather than cleaved. The taper provides several advantages in the detection of boundaries between immiscible fluids.

The light is initially bound inside the core of the optical fibre, but in the taper the angle the ray direction makes with the axis increases. Light on each mode escapes the core at some point in the taper which depends on the wavelength and the propagation mode involved. Then it propagates by reflecting at the taper walls. Depending on the index of the external medium, the light may be totally reflected at the cladding boundary. However, the propagation angle continues to steepen with each reflection until the axial component of the ray reverses and the light returns back up the fibre, becoming trapped again in the core by the reverse process. If the taper angle is small enough (below about 25 degrees for typical external fluids) the propagation angle in the taper can become greater than permits total reflection at the cladding boundary, and some reflections in the taper will depend on the external refractive index.

Because several reflections may occur which depend on the external index, and because the net reflection is the product of all individual reflections in a sequence, the tapered device can be more sensitive to the variations in the Fresnel reflection than if the fibre is untapered and the single end reflection is used. This is an unexpected result since it might be thought that the taper would result in less sensitive measurements due to the lower absolute value of the reflected signal. However, due to the increased number of reflections, the sensitivity is increased. In addition, the number of modes which are totally reflected is determined by the external index. Since the actual amount of light reflected will be smaller with the tapered sensor than with a single reflection, a sensitive instrument is needed to measure the reflection.

Analysis of reflected light from the end of a fibre sensor using frequency domain optical reflectometry is particularly effective for measurements of weak endreflections because it discriminates against continuous backscatter processes in the fibre and preferentially detects reflections which are discrete on the scale of the instrument resolution.

If the tapered region is short, and provided with a flat end, the light may be reflected from the end. The taper provides an advantage in this situation also, by presenting a surface of varying radius. Adhering droplets may be attracted to the region of smallest curvature, at the point where the taper begins, thus keeping the tip clear.

In one aspect, the invention provides an optical fibre sensor having a core and a cladding, in which the optical fibre sensor terminates in an end region, the improvement comprising: the diameter of the core diminishing monotonically over the end region such that propagation modes of the fibre become unbound from the core in the end region.

In another aspect, the invention provides an optical fibre sensor in which the improvement further comprises the cladding tapering over the end region.

In another aspect, the invention provide an optical fibre sensor in which the improvement further comprises the optical fibre sensor having a longitudinal axis and the end region terminating in a flat region perpendicular to the longitudinal axis.

In another aspect, the invention provides an optical fibre sensor in combination with an optical reflectometer, the optical reflectometer being optically connected to the optical fibre sensor to receive light propagating through the optical fibre sensor.

In another aspect, the invention provides an optical fibre sensor in which the improvement further comprises the taper walls of the end region being coated with a reflective material.

BRIEF DESCRIPTION OF THE FIGURES

There will now be described preferred embodiments of the invention, with reference to the figures by way of example, in which like numerals denote like features, and in which:

FIG. 1 shows a schematic cross-section of an embodiment of a tapered fibre sensor according to the invention;

FIG. 2 shows a schematic cross-section of a further embodiment of a tapered fibre sensor according to the invention;

FIG. 9 shows a schematic cross-section of an embodiment of a tapered fibre sensor according to the invention immersed in a fluid with adhering droplets of another fluid; and FIG. 10 shows a schematic cross-section of a further embodiment of a tapered fibre sensor according to the invention immersed in a fluid with adhering droplets of another fluid.

DESCRIPTION OF PREFERRED EMBODIMENTS

Figure 3:
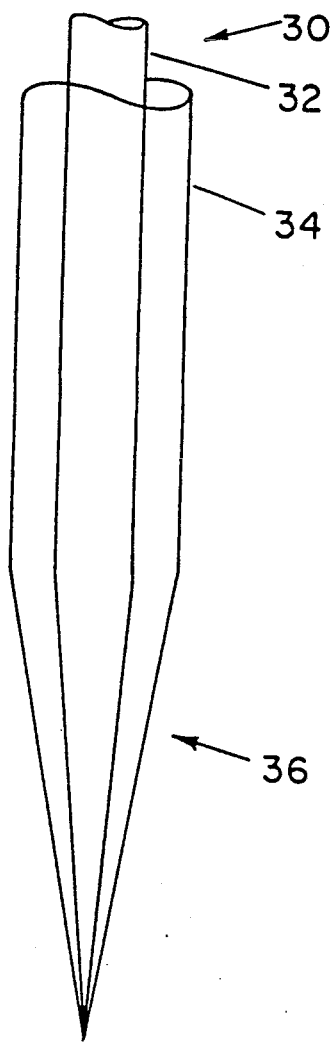
FIG. 3 shows a schematic cross-section of a further embodiment of a tapered fibre sensor according to the invention.

In this patent, optical fibre means an optical waveguide capable of transmitting light over at least the distances required for an optical sensor without undue propagation losses. Such an optical fibre shall be referred to as an optical fibre or a standard optical fibre, and will be composed of a core and a cladding each having refractive index distributions such that light propagates readily in the optical fibre.

The longitudinal axis of the optical fibre is the direction along which the light generally propagates. The taper angle of the optical fibre is the angle between the longitudinal axis and the surface of the tapering part of the optical fibre measured parallel to the longitudinal axis.

The end region of the optical fibre is the part of the optical fibre near its end closely adjacent where propagating modes of light may interact with the external medium. Closely adjacent means close enough such that propagating modes of light will have angles of reflection with the core and cladding interface such that the propagating modes become unbound in the part where the propagating modes may interact with the external medium.

The external medium is the medium whose index of refraction is being measured by the fibre sensor.

FIGS. 1-6 show configurations of the tapered optical fibre believed to have greatest utility. FIG. 1 shows a tapered fibre 10 whose core 12 and cladding 14 both taper over the end region 16. The extreme end 18 of the optical fibre has a cleaved or polished face perpendicular to the longitudinal axis of the optical fibre 10. Such a device can be made by softening the glass with heat and stretching it. For example, it may be made manually by pulling down a fibre in the arc of a fusion splicer by means of a micromanipulator to a taper angle of about 20 degrees, and cleaving the neck of the taper so that there is a planar end of about 25 micron diameter. It would be possible to make the flat end as a bulbous or otherwise curved end, but the operation would be essentially the same as for a flat end.

FIG. 2 shows an optical fibre 20 whose cladding 24 tapers in to meet the core 22 in the end region 26, and the core 22 then tapers at the same angle (or it could be another angle). This optical fibre 20 can be made by etching the fibre or grinding and polishing.

Figure 4:
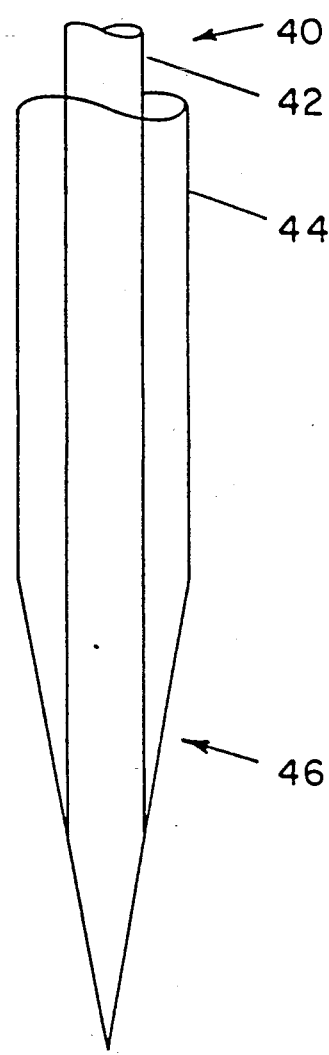
FIG. 4 shows a schematic cross-section of a further embodiment of a tapered fibre sensor according to the invention.
Figure 5:
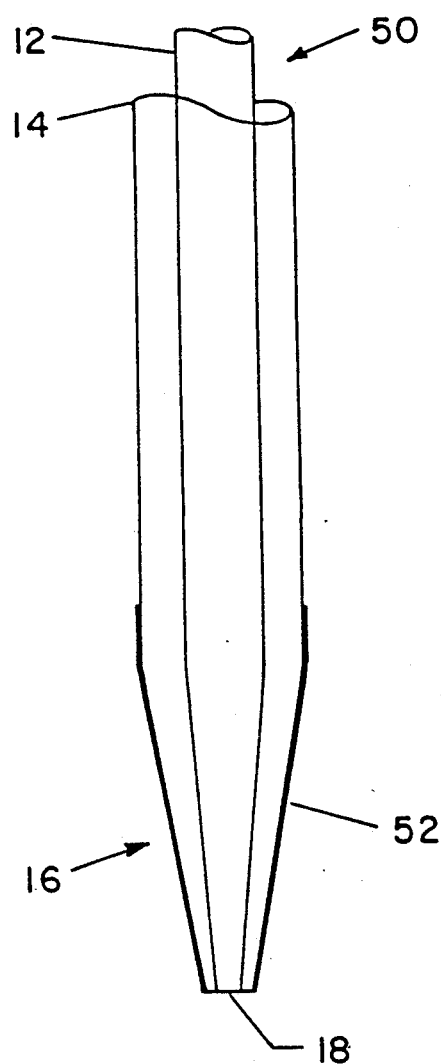
FIG. 5 shows a schematic cross-section of a further embodiment of a tapered fibre sensor according to the invention having a coated end surface.
Figure 6:
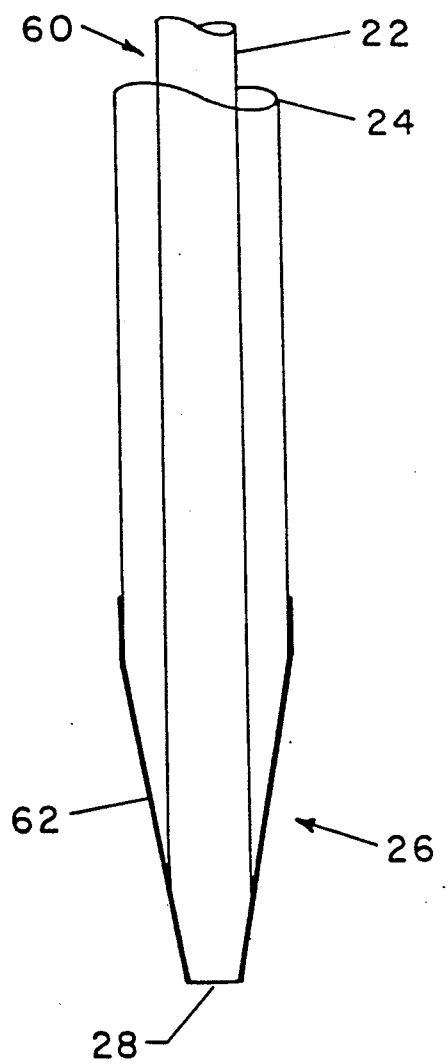
FIG. 6 shows a schematic cross-section of a further embodiment of a tapered fibre sensor according to the invention having a coated end surface.

FIGS. 5 and 6 show optical fibres 50 and 60 respectively having the same configurations as in FIGS. 1 and 2 but with the taper walls 52 and 62 respectively coated with an opaque substance, preferably a good reflector such as a metal, to keep the light inside in the tapered part. The coating extends along the optical fibres 50 and 60 respectively over the area where unbound propagating modes of light may interact with the external medium (not shown in FIGS. 1-6). The tapered fibres of FIGS. 1, 2, 5 and 6 are shown with flat ends 18 and 28.

The optical fibres 30 and 40 shown in FIGS. 3 and 4 are uncoated tapers with no flat end. Optical fibre 30 has a tapered core 32 and tapered cladding 34 over an end region 36 similar to that of optical fibre 10. Optical fibre 40 has a tapered core 42 and tapered cladding 44 over an end region 46 similar to optical fibre 20.

Figure 7:
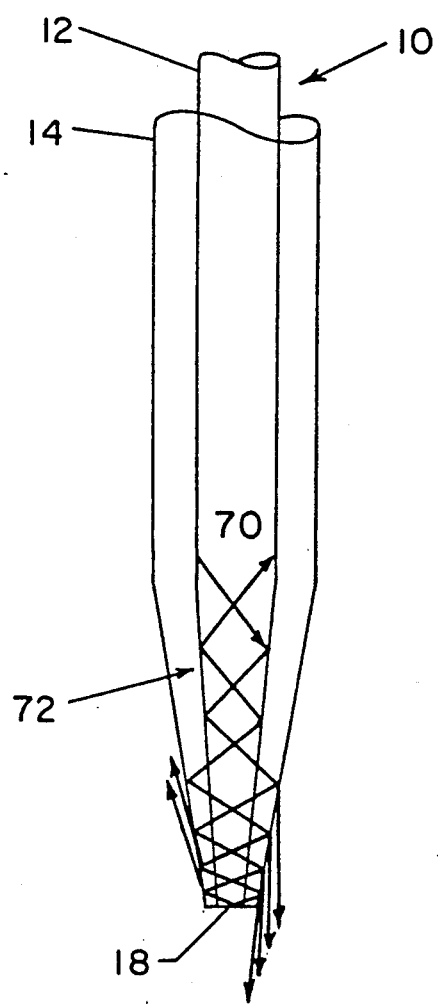
FIG. 7 shows a schematic cross-section of an embodiment of a tapered fibre sensor according to the invention showing light rays becoming unbound in the core taper.
Figure 8:
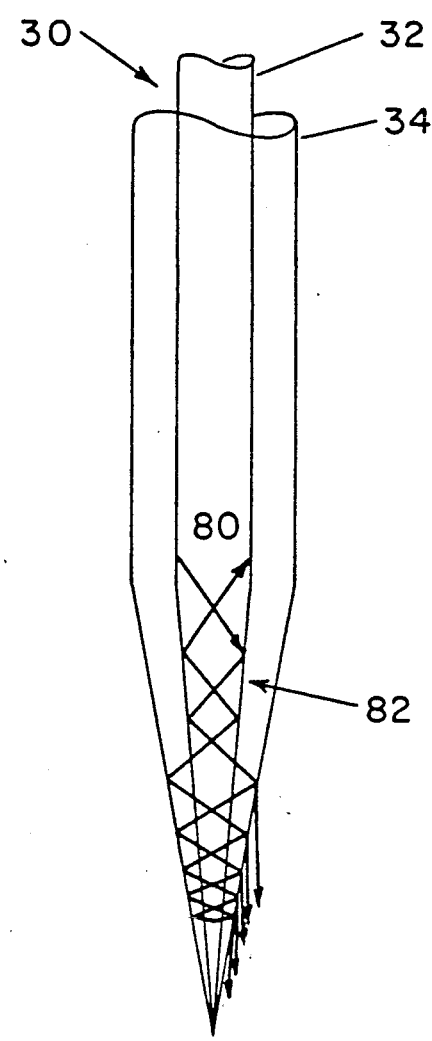
FIG. 8 shows a schematic cross-section of an embodiment of a tapered fibre sensor according to the invention having a pointed end showing light rays becoming unbound in the core taper.

FIGS. 7 and 8 show schematically a ray path through the optical fibres 10 and 30 respectively. The light is initially bound inside the core at 70 and 80 respectively, but with each bounce the angle the ray direction makes with the axis increases. Light on each mode escapes the core at some point (for example at 72 and 82 respectively) in the taper which depends on the wavelength and the propagation mode involved. Then it propagates by reflecting off the taper walls. Depending on the index of the external medium (not shown) the light may be totally reflected at the cladding boundary with the external medium. However, the propagation angle continues to steepen with each reflection and eventually the reflection becomes a partial one, the amount reflected depending on the external index. As the bounce angle steepens, the axial component of the ray reverses and the light returns back up the fibre, becoming trapped again in the core by the reverse process. The occurrence of partial reflections that depend on the external index requires sufficiently small taper angles (below about 25 degrees for typical external fluids).

The same processes occur in the taper of the etched type of optical fibre sensor shown in FIG. 2, but the mode remains in the core, and reflects from the core-ambient boundary (interface between the core and the external medium).

Because several reflections may occur which depend on the external index, and because the net reflection is the product of all individual reflections in a sequence, the tapered device can be more sensitive to the variations in the Fresnel reflection than if the fibre sensor is untapered and the single end reflection is used. This sensitivity can be used to remove an ambiguity that occurs when refractive index is measured at normal incidence. In addition the number of modes which are totally reflected is determined by the external index. The actual amount of light reflected, however, will be smaller with the tapered sensor than with a single reflection, and a sensitive instrument such as an frequency domain optical reflectometer (known in the art) is needed to measure the reflection. Frequency domain optical reflectometers are described in R. I. MacDonald, "Frequency Domain Optical Reflectometer", Applied Optics 20, pp. 1840-1844, the content of which is incorporated herein by reference in its entirety.

If the tapered region is short, and provided with a flat end, the light may be reflected from the flat end as well as the taper walls, as shown in FIG. 7.

FIGS. 9 and 10 show the optical fibre sensors 10 and 20 immersed in a fluid or external medium 92, with adhering droplets 94 of another fluid. For the purpose of detecting a change in the ambient index the tapered optical fibre sensors 10 and 20 have reduced susceptibility to contamination because contaminating fluid would have to cover the entire tapered region to overcome entirely the dependence of the reflection on the index of the ambient fluid.

Certain fluids will have a tendency to accumulate on the portions of the fibre which are least strongly curved (as at the beginning of the taper), to minimize the energy of the fluid boundary. This process can keep the end of the taper uncontaminated and thus provide a reliable end reflection if the taper is sufficiently short that a reflection can occur at a flat surface at the end. The optical fibre sensors 50 and 60 shown in drawings 5 and 6 have flat ends 18 and 28 respectively and coatings which constrain the mode to remain inside the taper. These sensors use only the end reflection, and rely on the self cleaning tendency property of the tapered shape. Although the modulation of the reflection by the taper wall is lost, they are advantageous if the index of a fluid to be sensed is greater than the index of the sensor at the boundary. In such a situation multiple reflections at the taper wall may reduce the reflection level below what can be detected.

There is no specific relationship required between the core and cladding refractive indices other than that the cladding index must be less than the core index as in any optical fibre dielectric waveguide and that the cladding index must be greater than the index of the fluids to be sensed. The latter restriction does not apply to the coated taper version shown in FIGS. 5 and 6.

In this patent, an optical fibre is a standard optical fibre, well known in the art, and it is believed that any standard fibre can be used with the taper of the invention.

The fibre used with the taper of the invention would preferably be a multimode fibre, of either the step or the graded index type. A monomode fibre would work similarly, with the difference that the mechanism modulating the number of modes leaking out would not operate, since only one is present.

The core and cladding taper need not be related in any way. In one aspect of the invention, only the core taper is necessary. If a core taper could be prepared inside a cylindrical cladding, the device would work as described, but present manufacturing techniques do not readily permit the construction of such a fibre. A cylindrical shape with an internal tapering core would be the same as a simple cleaved fibre for collecting fluid contamination on the end. However, since the internal taper makes the modes come out and hit the walls of the cylindrical cladding, the light can interact with the ambient medium at the cladding boundary even though the end is contaminated. The sensor with the external taper operates in this mode as well as described above.

It is important that the extraction of the light from the core occur over a portion of the length near the tip so that the light can interact with the external medium along the length of the fibre as well as at the end. The shape of the end surface itself is not strongly influential. The coated fibre version is an exception to this comment, to deal with the particular situation of external index higher than the cladding index.

I claim:

1. In an optical fibre sensor for measuring the index of refraction of an external medium, the optical fibre sensor having a core and a cladding, and the cladding having a refractive index greater than the index of the external medium, in combination with an optical reflectometer, the optical reflectometer being optically connected to the optical fibre sensor to receive light propagating through the optical fibre sensor: the improvement comprising the optical fibre sensor terminating in an end region, and the diameter of the core diminishing monotonically over the end region such that propagation modes of the fibre become unbound in the end region.

2. The optical fibre sensor of claim 1 in which the cladding tapers over the end region.

3. The optical fibre sensor of claim 1 in which the taper has a taper angle and the taper angle is less than 25 degrees.

4. The optical fibre sensor of claim 1 in which the taper has a taper angle and the taper angle is about 20 degrees.

5. The optical fibre sensor of claim 1 in which the optical fibre sensor has a longitudinal axis and the end region terminates in a flat region perpendicular to the longitudinal axis.

6. In the optical fibre sensor of claim 5, the improvement further comprising the end region being coated with a reflective material.

7. The optical fibre sensor of claim 1 in which the optical fibre sensor terminates in a point.

8. In the optical fibre sensor of claim 7, the improvement further comprising the end region being coated with a reflective material.

* * * * *